US012779183B2

(12) United States Patent
Fuma et al.

(10) Patent No.: US 12,779,183 B2
(45) Date of Patent: Nov. 3, 2026

(54) BALLOON CATHETER

(71) Applicant: KANEKA CORPORATION, Osaka (JP)

(72) Inventors: Yutaka Fuma, Settsu (JP); Chinami Takashima, Settsu (JP)

(73) Assignee: KANEKA CORPORATION, Osaka (JP)

( * ) Notice: Subject to any disclaimer, the term of this patent is extended or adjusted under 35 U.S.C. 154(b) by 176 days.

(21) Appl. No.: 18/835,216

(22) PCT Filed: Jan. 17, 2023

(86) PCT No.: PCT/JP2023/001210

§ 371 (c)(1),
(2) Date: Aug. 1, 2024

(87) PCT Pub. No.: WO2023/157534

PCT Pub. Date: Aug. 24, 2023

(65) Prior Publication Data

US 2025/0152922 A1 May 15, 2025

(30) Foreign Application Priority Data

Feb. 18, 2022 (JP) ................................ 2022-023390

(51) Int. Cl.
*A61M 25/10* (2013.01)
*A61M 25/00* (2006.01)

(52) U.S. Cl.
CPC ........ *A61M 25/10* (2013.01); *A61M 25/0045* (2013.01); *A61M 2025/0046* (2013.01)

(58) Field of Classification Search
CPC .......... A61M 25/0023; A61M 25/0029; A61M 25/0032; A61M 2025/0024;
(Continued)

(56) References Cited

U.S. PATENT DOCUMENTS 5,669,880 A * 9/1997 Solar ........................ A61F 2/958
604/103.1
2002/0002353 A1 * 1/2002 Michal .................. A61L 29/048
623/1.25

(Continued)

FOREIGN PATENT DOCUMENTS

JP 2010-119776 A 6/2010

OTHER PUBLICATIONS

International Search Report for PCT/JP2023/001210 (PCT/ISA/210) mailed on Mar. 7, 2023.

(Continued)

*Primary Examiner* — Kathleen S Holwerda
(74) *Attorney, Agent, or Firm* — Birch, Stewart, Kolasch & Birch, LLP

(57) ABSTRACT

Provided is a balloon catheter that can improve the sliding property of the guidewire. A balloon catheter having a shaft (10) having a lumen (100) including a first lumen (110) through which a guidewire (50) is to be inserted and a second lumen (120), a balloon disposed at a distal part of the shaft (10), and a tube disposed in the second lumen (120), wherein the first lumen (110) and the second lumen (120) are in communication with each other, the shaft (10) has a restriction part (40) preventing the tube (20) from moving from the second lumen (120) to the first lumen (110), the balloon catheter has a gap (200) between the tube (20) and the second lumen (120), and the total length $W_{200}$ of the gap (200) is shorter than or equal to the length $W_{20}$ of the tube (20) on the straight line L2.

12 Claims, 5 Drawing Sheets

(58) Field of Classification Search
CPC .. A61M 2025/0025; A61M 2025/0037; A61M 25/10; A61M 25/1025; A61M 25/104; A61M 2025/1056; A61M 2025/1061; A61M 2025/1063; A61B 2017/22001
See application file for complete search history.

(56) References Cited

U.S. PATENT DOCUMENTS

| | | | | |
|---|---|---|---|---|
| 2004/0254528 | A1* | 12/2004 | Adams .............. | A61M 25/0029<br>604/96.01 |
| 2009/0270801 | A1* | 10/2009 | Shimada ........... | A61M 25/0029<br>604/533 |

OTHER PUBLICATIONS

Written Opinion of the International Searching Authority for PCT/JP2023/001210 (PCT/ISA/237) mailed on Mar. 7, 2023.

* cited by examiner

[FIG. 1]
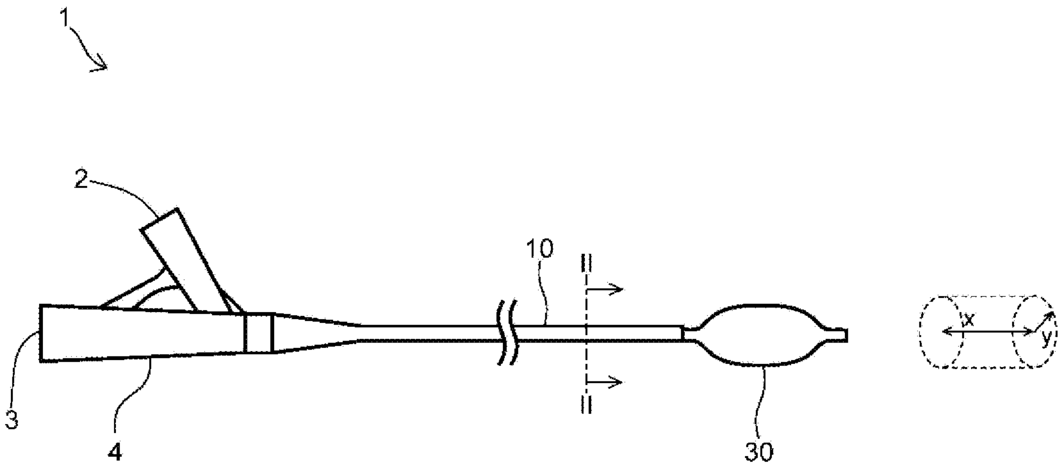
[FIG. 2]
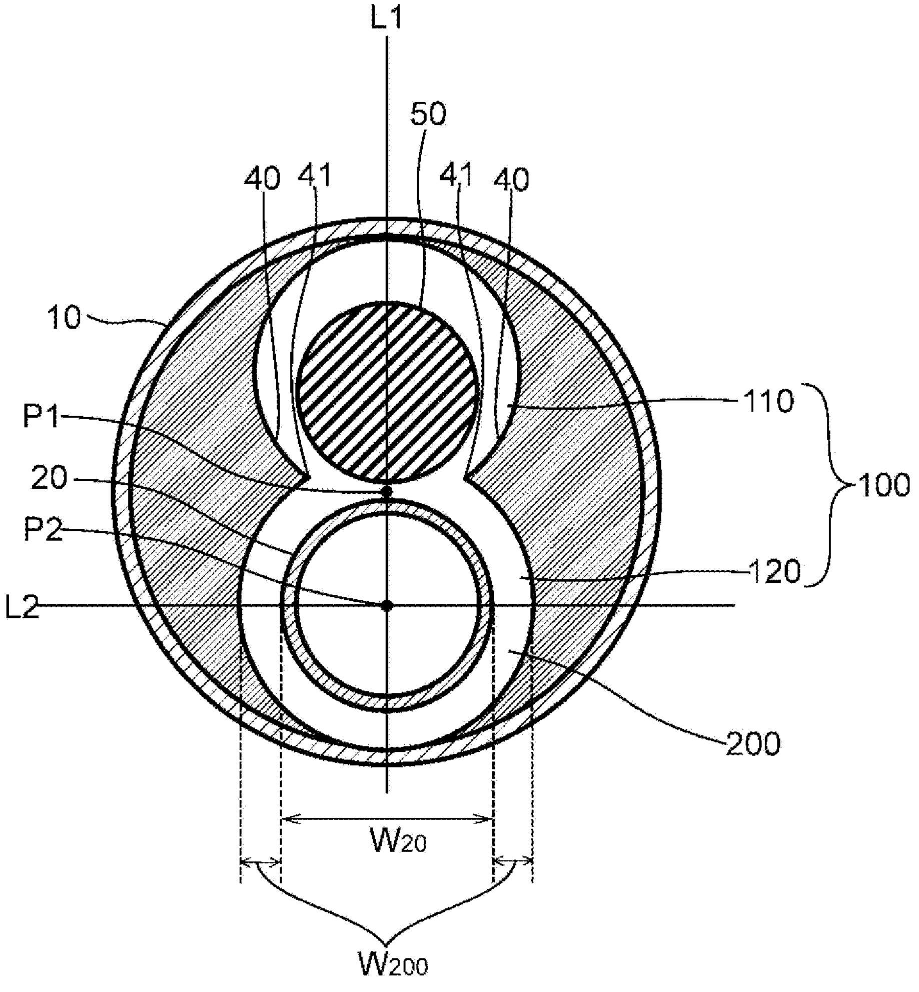

[FIG. 3]
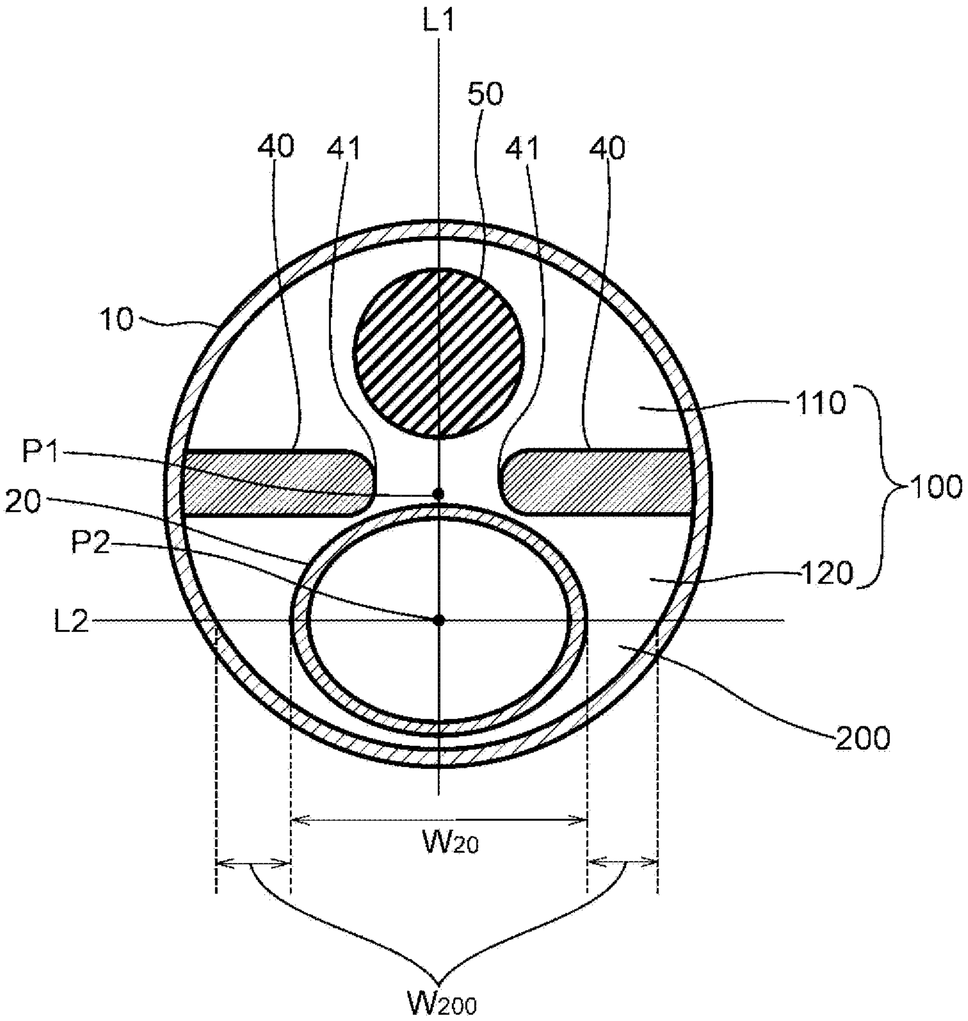

[FIG. 4]
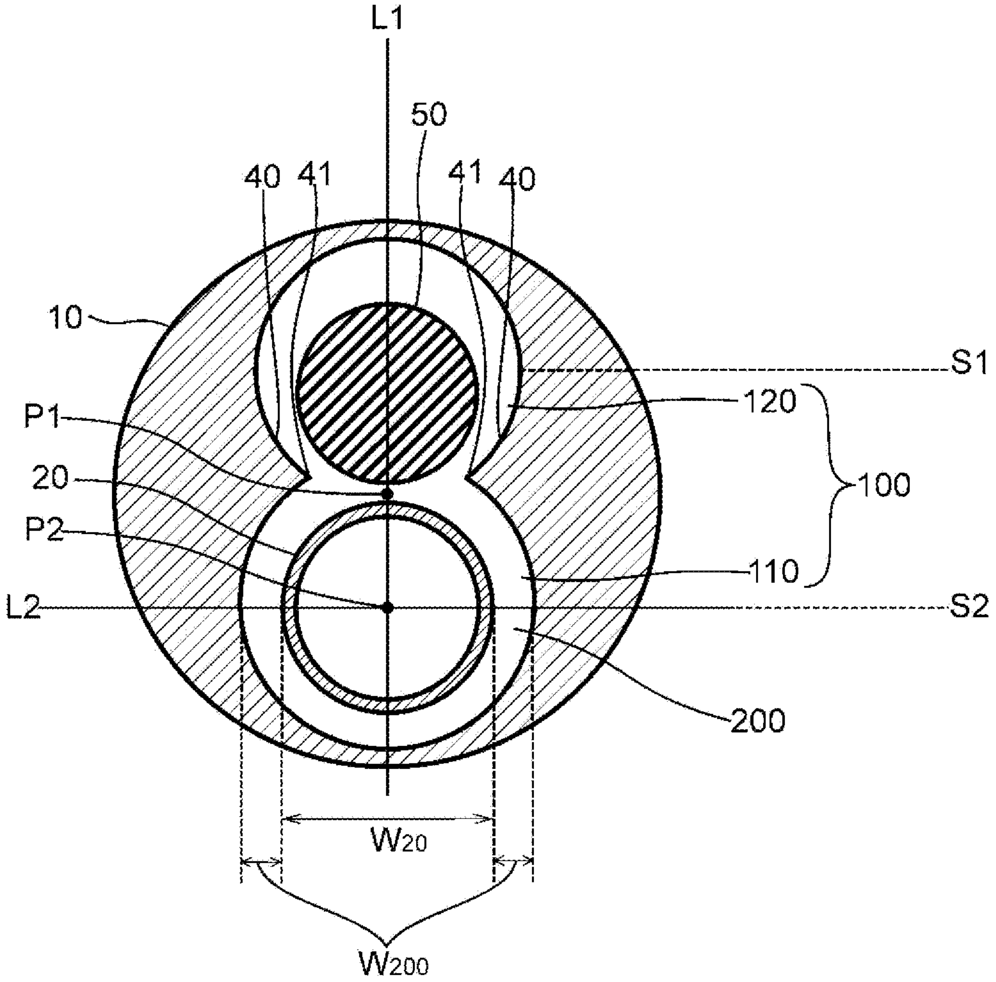

[FIG. 5]
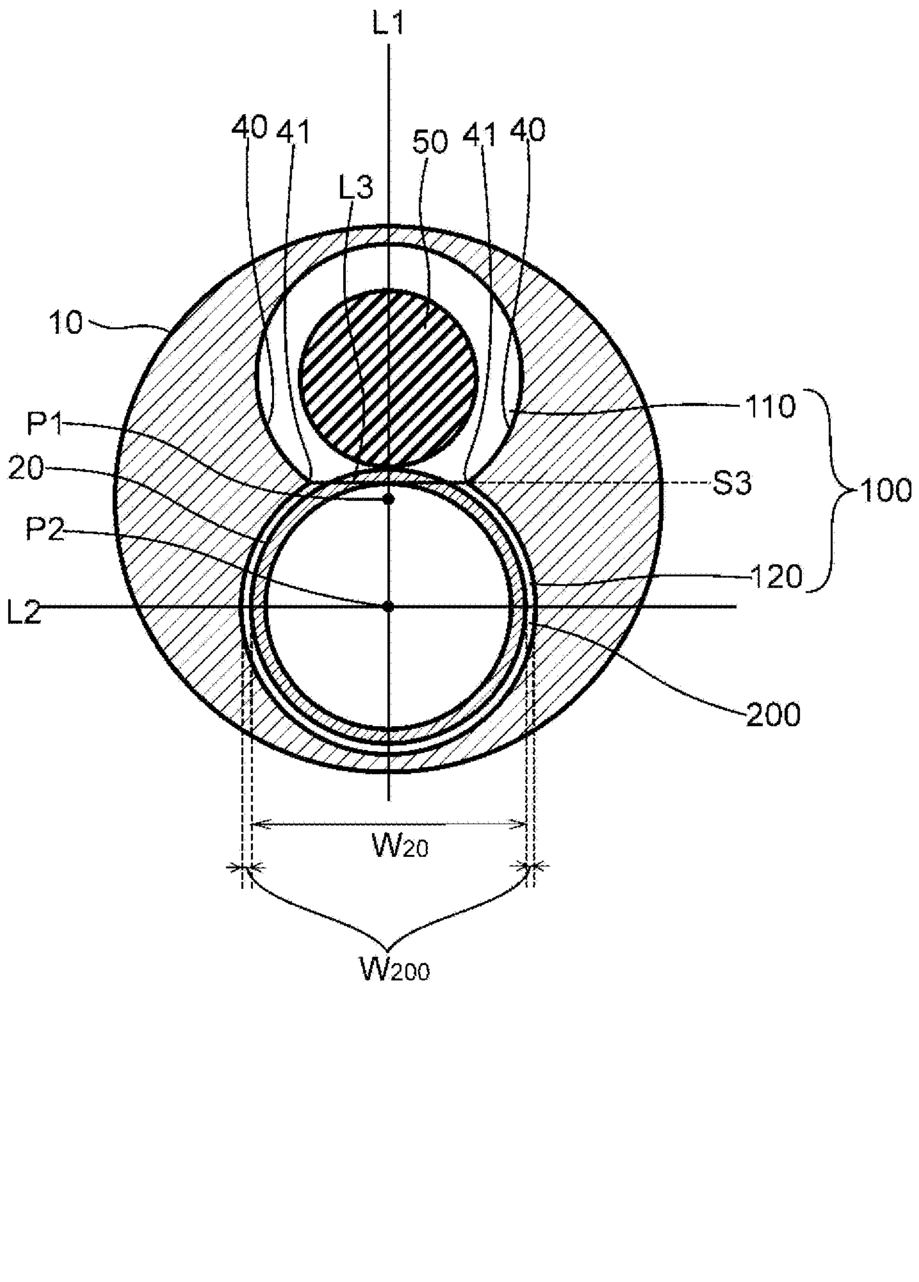

[FIG. 6]
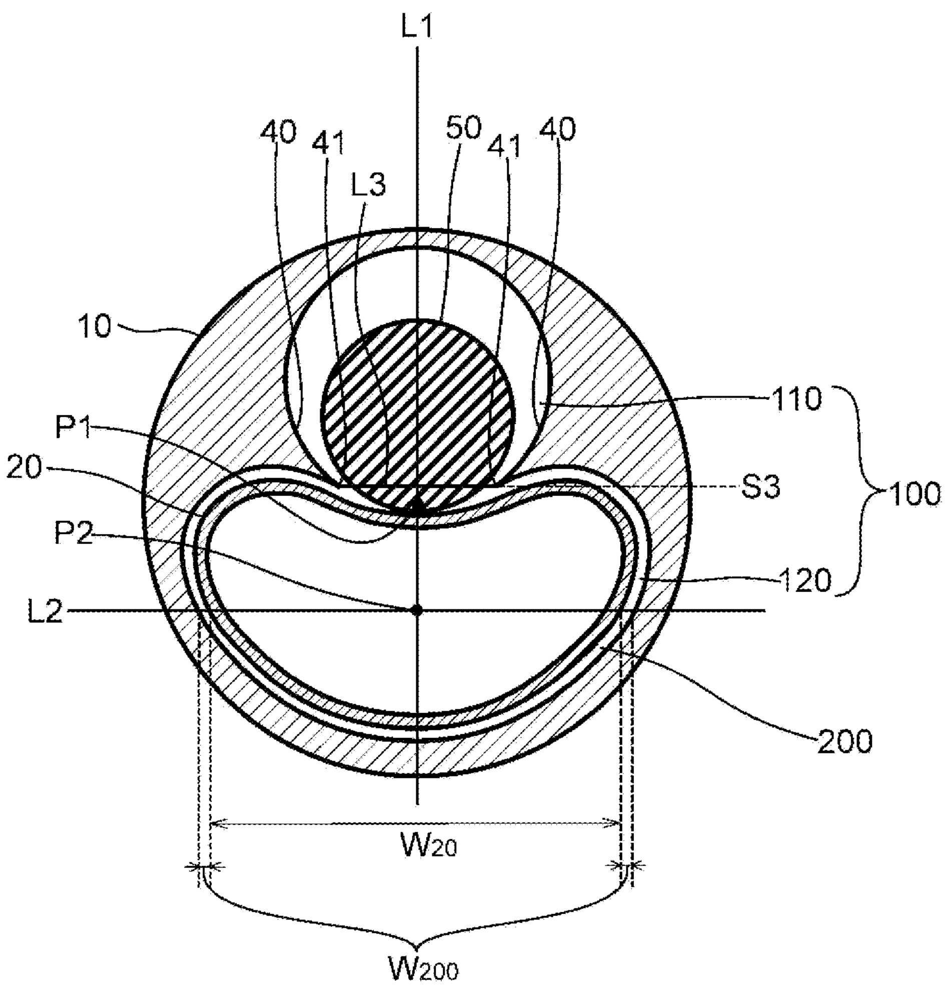

BALLOON CATHETER

TECHNICAL FIELD

The present invention relates to a balloon catheter.

BACKGROUND ART

Diseases such as angina pectoris and myocardial infarction are caused by the formation of stenotic areas hardened by calcification and other factors in inner walls of blood vessels. One of the treatments for these diseases is angioplasty, in which balloon catheter is used to dilate the stenotic area, such as percutaneous transluminal coronary angioplasty (PTCA) and percutaneous transluminal angioplasty (PTA). The angioplasty is a minimally invasive therapy that does not require an open chest procedure like bypass surgery and is widely used.

Balloon catheters used for angioplasty generally has a configuration where a balloon that can be inflated or deflated by adjusting the internal pressure is attached to the end of the shaft, and the shaft has a lumen through which a guidewire is inserted and a lumen that supplies fluid to adjust the internal pressure of the balloon. In angioplasty, the guidewire is first inserted into the vessel and advanced until the distal end of the guidewire passes beyond the target site for treatment. The balloon is inserted into the vessel along the guidewire, and when the balloon is delivered to the target site for treatment, the balloon is inflated by introducing fluid to dilate the vessel with the balloon. After the procedure, the balloon is deflated by removing the fluid from the balloon and removed from the body.

In a series of operations, the catheter needs to be pushed forward through curved or narrowed sections of the blood vessels. To achieve this, the ability to efficiently transmit the operation at the hand side to the distal side and push the catheter forward (pushability) and the ability to smoothly deliver the catheter along the guidewire (trackability) are required.

For example, Patent document 1 discloses a catheter support used with a therapeutic catheter and having a shaft portion shaped to limit radial movement of the therapeutic catheter over a certain length in the axial direction, thereby suppressing flexure of the therapeutic catheter and improving pushability of the therapeutic catheter in the axial direction.

RELATED ART DOCUMENT

Patent Document

Patent Document 1: JP-A-2010-119776

SUMMARY OF THE INVENTION

Problems to be Solved by the Invention

When performing procedures with a balloon catheter, a guidewire is first inserted into the blood vessel before the balloon, advancing the vessel through curved or narrowed sections of the vessel until reaching the target site for treatment. Subsequently, the balloon is delivered to the target site for treatment along the guidewire that has been placed the target site for the treatment. Performing this maneuver swiftly and safely enhances the safety and efficiency of the procedure with the balloon catheter. To achieve this, the guidewire inserted along the longitudinal axis direction of the shaft of the balloon catheter needs to be able to slide smoothly within the shaft. However, conventional balloon catheters have room for improvement in terms of the guidewire's sliding property within the shaft.

In view of the above circumstances, the object of this invention is to provide a balloon catheter that can improve the sliding property of the guidewire.

Means for Solving the Problems

A balloon catheter in accordance with one embodiment of the present invention that can solve the above problem is as follows.

[1] A balloon catheter having a distal end and a proximal end in a longitudinal axis direction, comprising: a shaft having a lumen and extending in the longitudinal axis direction, the lumen of the shaft including a first lumen through which a guidewire is to be inserted and a second lumen extending in the longitudinal axis direction; a balloon disposed at a distal part of the shaft; and a tube disposed in the second lumen, wherein in a cross-section perpendicular to the longitudinal axis direction, the first lumen and the second lumen are in communication with each other; the shaft has a restriction part preventing the tube from moving from the second lumen to the first lumen; the balloon catheter has a gap between an outer wall of the tube and a wall of the second lumen, wherein the gap is in communication with the first lumen, and the gap is formed by the outer wall of the tube and the wall of the second lumen not coming into contact with each other; and in a cross-section perpendicular to the longitudinal axis direction, L1 is a straight line connecting a figure center P1 of an outer edge of the shaft and a figure center P2 of an outer edge of the tube, L2 is a straight line passing through the figure center P2 and being perpendicular to the straight line L1, and a total length of the gap is shorter than or equal to a length defined by the outer edge of the tube on the straight line L2.

The shaft has the restriction part that restricts the tube from moving from the second lumen to the first lumen, and the gap between the tube and the second lumen meets the above requirements, thereby preventing the tube located in the second lumen of the lumen of the shaft from moving toward the first lumen through which the guidewire is to be inserted. This can prevent entanglement of the guidewire with the tube and improve sliding property of the guidewire in the shaft. The balloon catheter is flushed with saline solution before use, and then the saline solution is drained out for treatment. The gap that meets the above requirements is formed on the outside of the tube, so that the saline solution after flushing is retained in the gap. This retained water seeping into the first lumen can lubricate the guidewire inserted into the first lumen, and thus improve the sliding property of the guidewire.

The balloon catheter in accordance with embodiments of the present invention is preferably the following [2] to [10].

[2] The balloon catheter according to [1], wherein in a cross-section perpendicular to the longitudinal axis direction, a first position is defined as a position where the largest diameter of the first lumen is located and a second position is defined as a position where the largest diameter of the second lumen is located in a direction parallel to the straight line L2, and the restriction part is formed by a thicker wall thickness of the shaft between the first position and the second position than a wall thickness of the shaft at the second position.

[3] The balloon catheter according to [1] or [2], wherein the shaft and the tube are formed from different materials.

[4] The balloon catheter according to any one of [1] to [3], wherein a stiffness of the tube is higher than a stiffness of the shaft.

[5] The balloon catheter according to any one of [1] to [3], wherein a stiffness of the tube is lower than a stiffness of the shaft.

[6] The balloon catheter according to any one of [1] to [5], wherein in a cross-section perpendicular to the longitudinal axis direction, the shaft has a third position where the lumen of the shaft is at its minimum width in a direction parallel to the straight line L2 by the restriction part, L3 is a line segment connecting opposing inner walls of the lumen of the shaft at the third position and being parallel to the straight line L2, and the outer edge of the tube either contacts the line segment L3 or has a portion located on the opposite side of the figure center P2 with respect to the line segment L3.

[7] The balloon catheter according to any one of [1] to [5], wherein in a cross-section perpendicular to the longitudinal axis direction, the shaft has a third position where the lumen of the shaft is at its minimum width in a direction parallel to the straight line L2 by the restriction part, L3 is a line segment connecting opposing inner walls of the lumen of the shaft at the third position and being parallel to the straight line L2, and the outer edge of the tube does not have a portion located on the opposite side of the figure center P2 with respect to the line segment L3.

[8] The balloon catheter according to any one of [1] to [7], wherein a portion of the outer wall of the tube facing the first lumen is provided with a hydrophilic or hydrophobic coating.

[9] The balloon catheter according to any one of [1] to [8], wherein an inner wall of the shaft forming the first lumen is provided with a hydrophilic or hydrophobic coating.

[10] The balloon catheter according to any one of [1] to [9], wherein an inner wall of the tube is provided with a hydrophilic or hydrophobic coating.

Effects of the Invention

According to the above balloon catheter, the sliding property of the guidewire that is to be inserted into the first lumen of the shaft can be improved. This enables the rapid and safe performance and procedures such as delivering the guidewire to the treatment site prior to the balloon, and delivering the balloon to the treatment site along the guidewire after the guidewire is delivered. As a result, the safety and efficiency of the balloon catheter procedure can be improved.

BRIEF DESCRIPTION OF THE DRAWINGS

FIG. 1 is a side view of a balloon catheter in accordance with an embodiment of the present invention.

FIG. 2 is a cross-sectional view along the II-II line of FIG. 1.

FIG. 3 is another example of the cross-sectional view of FIG. 2.

FIG. 4 is a cross-sectional view of a balloon catheter perpendicular to the longitudinal axis direction in accordance with another embodiment of the present invention.

FIG. 5 is another example of the cross-sectional view of FIG. 4.

FIG. 6 is still another example of the cross-sectional view of FIG. 4.

MODE FOR CARRYING OUT THE INVENTION

Hereinafter, the present invention will be described based on the following embodiments, however, the present invention is not limited by the following embodiments and can be altered in design within a scope in compliance with the intent described above and below, and all the changes are to be encompassed within a technical scope of the present invention. Note that, in each drawing, hatching, reference signs for components, and the like may be omitted for convenience of description, and in such a case, the specification and other drawings are to be referred to. Furthermore, since the dimensions of the various components in the drawings are provided for the purpose of facilitating the understanding of the feature of the present invention, the dimensions may differ from the actual dimensions in some cases.

Referring to FIG. 1 to FIG. 6, a balloon catheter in accordance with embodiments of the present invention will be described. Note that the present invention is not limited to the embodiments shown in the figures. FIG. 1 is a side view of a balloon catheter in accordance with an embodiment of the present invention. FIG. 2 is a cross-sectional view along the II-II line of FIG. 1, and FIG. 3 represents a variation of the cross-sectional view of FIG. 2. FIG. 2 and FIG. 3 show embodiments in which the shaft and the restriction part are composed of different parts. FIG. 4 is a cross-sectional view of a balloon catheter perpendicular to the longitudinal axis direction in accordance with another embodiment of the present invention and shows an embodiment in which the restriction part is formed by the thick wall of the shaft. FIG. 5 and FIG. 6 represent another variation of the cross-sectional view of FIG. 4, respectively. The cross-sectional views of FIG. 2 to FIG. 6 show the state where the guidewire is inserted in the first lumen.

As shown in FIG. 1, a balloon catheter 1 in accordance with embodiments of the present invention has a distal end and a proximal end in a longitudinal axis direction x. The proximal end is an end on a proximal side in the longitudinal axis direction x, and the proximal side refers to the direction towards a user's hand in the extending direction of the balloon catheter 1, i.e., the longitudinal axis direction x. The distal end is an end on a distal side in the longitudinal axis direction x, and the distal side refers to the opposite side of the proximal side, that is, the direction towards the object to be treated. In a cross-section perpendicular to the longitudinal axis direction x, the direction connecting the figure center P1 of the outer edge of a shaft 10 and a point on the outer edge of the shaft 10 is defined as a radial direction y.

As shown in FIG. 1 to FIG. 3, the balloon catheter 1 has the shaft 10 having a lumen 100 and extending in the longitudinal axis direction x, the lumen 100 of the shaft 10 has a first lumen 110 through which a guidewire 50 is to be inserted and a second lumen 120 extending in the longitudinal axis direction x; a balloon 30 disposed at a distal part of the shaft 10; and a tube 20 disposed in the second lumen 120.

The tube 20 is preferably a flow path for fluid that is introduced when the balloon 30 is inflated and discharged when it is deflated. The fluid can be introduced or discharged using an indeflator (pressurizer for balloons) to control the inflation and deflation of the balloon 30. The fluid may be a pressurized fluid pressurized by a pump or the like.

The balloon catheter 1 with the balloon 30 disposed at a distal part of the shaft 10 can be configured with a distal part of the tube 20 disposed in the second lumen 120 of the shaft 10 connected to a proximal end part of the balloon 30. The distal part of the tube 20 and the proximal end part of the balloon 30 may be joined by adhesive bonding, welding, or by attaching a ring-shaped member at the point where the distal part of the tube 20 and the proximal end part of the balloon 30 overlap to swage them. Of these, the tube 20 and the balloon 30 are preferably joined by welding. By welding the tube 20 and the balloon 30, the bond between the tube 20 and the balloon 30 is difficult to be released even when the balloon 30 is repeatedly inflated and deflated, easily increasing the strength of the bond between the tube 20 and the balloon 30.

As shown in FIG. 2 and FIG. 3, in a cross-section perpendicular to the longitudinal axis direction x, the first lumen 110 and the second lumen 120 are in communication with each other, and the shaft 10 has a restriction part 40 preventing the tube 20 from moving from the second lumen 120 to the first lumen 110.

The balloon catheter 1 has a gap 200 between an outer wall of the tube 20 and a wall of the second lumen 120, wherein the gap 200 is in communication with the first lumen 110, and the gap 200 is formed by the outer wall of the tube 20 and the wall of the second lumen 120 not coming into contact with each other; and in a cross-section perpendicular to the longitudinal axis direction x, L1 is a straight line connecting a figure center P1 of an outer edge of the shaft 10 and a figure center P2 of an outer edge of the tube 20, L2 is a straight line passing through the figure center P2 and being perpendicular to the straight line L1, and a total length $W_{200}$ of the gap 200 is shorter than or equal to a length $W_{20}$ defined by the outer edge of the tube 20 on the straight line L2.

The restriction part 40 may be provided as a different member from the shaft 10 as shown in FIG. 2 and FIG. 3, or it may be provided by the thicker wall thickness of the shaft 10 as described below. In either case, the restriction part 40 is preferably provided so that the lumen 100 of the shaft 10 is narrowed in the direction of the straight line L2 by the restriction part 40 when the straight line connecting the figure center P1 of the outer edge of the shaft 10 and the figure center P2 of the outer edge of the tube 20 is L1, and the straight line passing through the figure center P2 and being perpendicular to the straight line L1 is L2. With this configuration, the restriction part 40 can prevent the tube 20 disposed in the second lumen 120 from moving from the second lumen 120 to the first lumen 110. As a result, a guidewire 50 that is to be inserted in the first lumen 110 and the tube 20 can be prevented from becoming entangled, thereby improving the sliding property of the guidewire 50.

Furthermore, the balloon catheter 1 has the gap 200 between the outer wall of the tube 20 and the wall of the second lumen 120, wherein the gap 200 is in communication with the first lumen 110, and the gap 200 is formed by the outer wall of the tube 20 and the wall of the second lumen 120 not coming into contact with each other, and in a cross-section perpendicular to the longitudinal axis direction x, L1 is a straight line connecting the figure center P1 of the outer edge of the shaft 10 and the figure center P2 of the outer edge of the tube 20, L2 is a straight line passing through the figure center P2 and being perpendicular to the straight line L1, and the total length $W_{200}$ of the gap 200 is shorter than or equal to the length $W_{20}$ defined by the outer edge of the tube 20 on the straight line L2. This configuration allows the size of the tube 20 relative to the size of the second lumen 120 to be more than a certain size in a cross-section perpendicular to the longitudinal axis direction x, thus preventing the tube 20 located in the second lumen 120 from escaping into the first lumen 110.

Preferably, the shaft 10 does not have a boundary that is provided between the first lumen 110 and the second lumen 120 in a manner that makes them independent from each other. This allows the first lumen 110 and the second lumen 120 to be in communication with each other. However, it is acceptable for the shaft 10 to have a boundary between the first lumen 110 and the second lumen 120 in part of the longitudinal axis direction x, provided that it does not have a boundary for most of the longitudinal axis direction x.

As shown in FIG. 2 and FIG. 3, since the shaft 10 does not have a boundary between the first lumen 110 and the second lumen 120, the first lumen 110 and the second lumen 120 are not independent lumens, and therefore, it can be said that the first lumen 110 and the second lumen 120 are parts of the lumen 100 of the shaft 10. In other words, the first lumen 110 is the part of the lumen 100 of the shaft 10 through which the guidewire 50 is to be inserted, and the second lumen 120 is the part of the lumen 100 of the shaft 10 in which the tube 20 is placed.

As shown in FIG. 2, the restriction part 40 is preferably formed so that the cross-sectional shapes of the first lumen 110 and the second lumen 120 perpendicular to the longitudinal axis direction x have a shape that includes a portion of a circular or oval shape, respectively. The cross-sectional shape of the second lumen 120 including a portion of a circular or oval shape allows the gap 200 formed between the outer wall of the tube 20 and the wall of the second lumen 120 to easily have the size in the above range by also making the outer shape of the tube 20 circular or oval. The cross-sectional shape of the first lumen 110 including a portion of a circular or oval shape makes it easier to insert the guidewire 50 into the first lumen 110, and the outer shape of the guidewire 50 can also be circular or oval, making it easier to reduce resistance between the guidewire 50 and the wall of the first lumen 110 and improve the sliding property of the guidewire 50.

Alternatively, as shown in FIG. 3, the restriction part 40 may be a protruding part projecting inwardly in the radial direction y from the inner wall of the shaft 10 so that the inner wall of the shaft 10 narrows in the direction of the straight line L2. Although FIG. 3 shows a protruding part projecting in the direction of the straight line L2, the projecting direction of the protruding part need not be parallel to the direction of the straight line L2 as long as the restriction part 40 is provided so that the inner wall of the shaft 10 is narrowed in the direction of the straight line L2. In this case, the cross-sectional shapes of the lumen 100 of the shaft 10 perpendicular to the longitudinal axis direction x is preferably circular or oval. The shaft 10 with a circular or oval cross-sectional shape allows the cross-sectional shape of the first lumen 110 on one side of the restriction part 40 and the second lumen 120 on the other side of the restriction part 40 to include a portion of a circular or oval shape, even when the restriction part 40 is provided as a protruding part, so that the guidewire 50 and the tube 20 can be easily arranged.

FIG. 2 and FIG. 3 show embodiments in which the restriction part 40 is provided on both sides of the lumen 100 of the shaft 10 in the radial direction y. However, the restriction part 40 may be provided only on one side in the radial direction y. From the viewpoint of increasing the effectiveness of restraining the movement of the tube 20 disposed in the second lumen 120 into the first lumen 110 and facilitating the placement of the tube 20 with a circular outer cross-sectional shape, the restriction part 40 is preferably provided on both sides in the radial direction y.

In the case where the restriction part 40 is provided as a different member from the shaft 10, the restriction part 40 is preferably fixed to the inner wall of the shaft 10. In this case, the lumen 100 of the shaft 10 refers to the space formed inside the restriction part 40 in the radial direction y. When the portion of the restriction part 40 projecting most inwardly in the radial direction y is defined as a most protruding portion 41, the restriction part 40 is preferably provided so that the first lumen 110 is formed on one side and the second lumen 120 is formed on the other side across the most protruding portion 41 in the direction of the straight line L1. In other words, in the direction of the straight line L1, preferably, the first lumen 110 is formed on one side on a line segment L3, which will be described later, and the second lumen 120 is formed on the other side of the line segment L3.

In the direction of the straight line L2 in a cross-section perpendicular to the longitudinal axis direction x, the width of the lumen 100 of the shaft 10 at the position where the most protruding portion 41 is located is preferably shorter than the length $W_{20}$ defined by the outer edge of the tube 20. Such a configuration can prevent the tube 20 from moving from the second lumen 120 to the first lumen 110.

As shown in FIG. 4, in a cross-section perpendicular to the longitudinal axis direction x, a first position S1 is defined as a position where the largest diameter of the first lumen 110 is located and a second position S2 is defined as a position where the largest diameter of the second lumen 120 is located in a direction parallel to the straight line L2, and the restriction part 40 may be formed by a thicker wall thickness of the shaft 10 between the first position S1 and the second position S2 than a wall thickness of the shaft 10 at the second position S2. This configuration allows the restriction part 40 to be formed as an integral part of the shaft 10, facilitating the manufacturing of the balloon catheter 1.

FIG. 4 shows an example in which the restriction part 40 is formed so that the cross-sectional shapes of the first lumen 110 and the second lumen 120 perpendicular to the longitudinal axis direction x, respectively, are approximately circular, but the shape of the restriction part 40 is not particularly limited as long as it satisfies the above requirements even in the case where the restriction part 40 is formed by a thicker thickness of the wall of the shaft 10.

While FIG. 4 shows an example in which the restriction part 40 is formed by a thicker thickness of the wall of the shaft 10 than the wall thickness of the shaft 10 at the second position S2 on both sides in the radial direction y, the restriction part 40 may be formed by a thicker thickness of the wall of the shaft 10 than the wall thickness of the shaft 10 at the second position S2 on one side in the radial direction y. From the viewpoint of increasing the effectiveness of preventing the tube 20 placed in the second lumen 120 from moving into the first lumen 110 and facilitating the placement of the tube 20 with a circular outer cross-sectional shape, the restriction part 40 is preferably formed on both sides in the radial direction y.

The lumen 100 of the shaft 10 of the balloon catheter 1 is flushed with saline solution before use, and then the saline solution is drained out from the lumen 100 of the shaft 10. At this time, the saline solution is discharged from the first lumen 110 among the lumen 100 of the shaft 10, but in the second lumen 120, the tube 20 is placed and the gap 200 is formed between the outer wall of the tube 20 and the wall of the second lumen 120, so the saline solution remains and is retained in the gap 200 due to capillary action. Since the first lumen 110 and the second lumen 120 are in communication with each other, the saline solution retained in the gap 200 seeps out of the gap 200 into the first lumen 110 during use of the balloon catheter 1, thereby lubricating the guidewire 50 that is inserted into the first lumen 110 and improving the sliding property of the guidewire 50. In addition, when viscous liquids such as contrast medium is passed through the lumen 100 of the shaft 10 after flushing, the moisture seeping from the gap 200 dilutes the concentration of the viscous liquids in the first lumen 110, and the effect of improved sliding property of the guidewire 50 can be obtained.

As shown in FIG. 2 to FIG. 4, in a cross-section perpendicular to the longitudinal axis direction x, the total length $W_{200}$ of the gap 200 on the straight line L2 is shorter than or equal to the length $W_{20}$ defined by the outer edge of the tube 20 on the straight line L2. The total length $W_{200}$ of the gap 200 is preferably 0.9 times or shorter the length $W_{20}$ defined by the outer edge of the tube 20, more preferably 0.8 times or shorter, and may be 0.7 times or shorter or 0.5 times or shorter. The lower limit of the total length $W_{200}$ of the gap 200 is not particularly limited, and preferably 0.02 times or longer the length $W_{20}$ defined by the outer edge of the tube 20, more preferably 0.05 times or longer, and even more preferably 0.1 times or longer. The total length $W_{200}$ of the gap 200 within the above range allows the saline solution to remain in the gap 200 due to capillary action. In addition, when the total length $W_{200}$ of the gap 200 is within the above range, the size of the tube 20 relative to the size of the second lumen 120 is greater than specified, thus preventing the tube 20 placed in the second lumen 120 from escaping into the first lumen 110.

As shown in FIG. 2 and FIG. 4, in a cross-section perpendicular to the longitudinal axis direction x, the gap 200 between the outer wall of the tube 20 and the wall of the second lumen 120 is preferably formed to have a uniform length in the circumferential direction of the tube 20. This makes it easier for the saline solution to remain in the gap 200 due to capillary action.

The shaft 10 is preferably made of a material that is both flexible and biocompatible, and the material used to form the shaft 10 includes, for example, polyamide-based resin, polyester-based resin, polyurethane-based resin, polyolefin-based resin, fluorine-based resin, polyvinyl chloride-based resin, silicone-based resin, and natural rubber. Only one of these may be used, or two or more may be used in combination. Of these, the material forming the shaft 10 is preferably at least one of polyamide-based resin, polyolefin-based resin, and fluorine-based resin. This can improve surface slipperiness of the shaft 10 and improve the insertion of the balloon catheter 1 into the body cavity.

In the case where the restriction part 40 is made of a different material from the shaft 10, the material constituting the restriction part 40 can be understood referring to the material constituting the shaft 10 described above. From the viewpoint of easy fixation of the shaft 10 and the restriction part 40, the material constituting the restriction part 40 is preferably the same as the material constituting the shaft 10. The shaft 10 and the restriction part 40 are preferably fixed by welding, adhesive bonding, or other means. In the case where the restriction part 40 is formed by a thicker wall thickness of the shaft 10, the shaft 10 with the restriction part 40 can be manufactured by using a mold having a shape that allows the formation of the first lumen 110 and the second lumen 120 when forming the shaft 10.

As shown in FIG. 1, the balloon 30 preferably has an inflatable part, a proximal sleeve part located proximal to the inflatable part, and a distal sleeve part located distal to the inflatable part. With such a configuration, at least part of the proximal sleeve part can be connected to the tube 20, and the inflatable part can be inflated by fluid introduced through the tube 20 to perform procedures such as vasodilatation. Preferably, the proximal and distal sleeve part do not inflate even in the inflated state of the inflatable part. This can ensure a stable connection between the balloon 30 and the tube 20, even in the inflated state of the balloon 30. The inflatable part of the balloon 30 may have a straight tubular part, a proximal tapered part located proximal to the straight tubular part, and a distal tapered part located distal to the straight tubular part.

Materials forming the balloon 30 include, for example, polyolefin-based resin such as polyethylene, polypropylene, ethylene-propylene copolymer; polyester-based resin such as polyethylene terephthalate and polyester elastomer; polyurethane-based resin such as polyurethane and polyurethane elastomer; polyphenylene sulfide-based resin; polyamide-based resin such as polyamide and polyamide elastomer; fluorine-based resin; silicone-based resin; and natural rubber such as latex rubber. Only one of these may be used, or two or more may be used in combination. Of these, polyamide-based resin, polyester-based resin, and polyurethane-based resin are preferably used. In particular, elastomer resin is preferably used from the viewpoint of thinning and flexibility of the balloon 30. For example, among polyamide-based resins, nylon 12, nylon 11, and the like are suitable for the resin forming the balloon 30, and more preferably nylon 12 because it is relatively easy to mold when blow molding.

The tube 20 is preferably a flow path for fluid that is introduced when the balloon 30 is inflated and discharged when it is deflated. The cross-sectional shape of the tube 20 perpendicular to the longitudinal axis direction x is preferably circular, oval, or a shape including parts thereof. Furthermore, the cross-sectional shape of the tube 20 perpendicular to the longitudinal axis direction x is preferably along the cross-sectional shape of the second lumen 120 perpendicular to the longitudinal axis direction x. This allows the gap 200 between the outer wall of the tube 20 and the wall of the second lumen 120 to be formed to have a uniform length in the circumferential direction of the tube 20 in a cross-section perpendicular to the longitudinal axis direction x, making it easier for the saline solution to remain in the gap 200 due to capillary action.

Materials forming the tube 20 include, for example, resins such as polyimide-based resin, polyamide-based resin, PEEK resin, polyester-based resin, polyolefin-based resin, fluorine-based resin, polyvinyl chloride-based resin, polyurethane-based resin, silicone-based resin; and metals such as nickel titanium alloy, cobalt chromium alloy, tungsten alloy, titanium, stainless steel. Of these, the tube 20 is preferably made of metal. When the tube 20 is made of metal, the tube 20 can improve the stiffness of the shaft 10, even if the shaft 10 does not have a boundary that is provided between the first lumen 110 and the second lumen 120 to separate them from each other independently. This can improve the pushability of the balloon catheter 1. In addition, since the tube 20 is placed in the second lumen 120 of the shaft 10, the tube 20 is located closer to one side with respect to the central axis of the shaft 10, thereby improving torque transmission whereby rotational forces applied at the hand side are transmitted to the distal side. Furthermore, the tube 20 made of metal can easily provide the shaft 10 with more stiffness than prescribed, even if the outer shape of the shaft 10 is reduced, thereby improving the trackability of the balloon catheter 1.

In the balloon catheter 1, the shaft 10 and the tube 20 are preferably formed from different materials. With the shaft 10 and the tube 20 formed from different materials, the outer diameter and stiffness of the balloon catheter 1 can be adjusted by configuring the tube 20 with the material for desired purposes. As a result, it is possible to make the balloon catheter 1 with the desired pushability, trackability, and torque transmission.

The tube 20 may be constructed from different materials in the longitudinal axis direction x. For example, the central part of the tube 20 may be made of metal, and the distal end part and/or proximal end part of the tube 20 may be made of resin. In this configuration, the central part of the tube 20 in the longitudinal axis direction x has high stiffness due to the metal, while the end of the tube 20, which is connected to the balloon 30 or the like, is made of resin to facilitate the connecting of the tube 20 with the balloon 30 and the like.

The stiffness of the tube 20 is preferably higher than the stiffness of the shaft 10. The stiffness of the tube 20 can be made higher than the stiffness of the shaft 10 by constructing the shaft 10 from resin and the tube 20 from metal, or by constructing the tube 20 from a resin that can provide higher stiffness than the resin constituting the shaft 10. Alternatively, even if the shaft 10 and the tube 20 are made from the same material, the stiffness of the tube 20 can be made higher than the stiffness of the shaft 10 by structural differences such as making the wall thickness of the tube 20 thicker than the wall thickness of the shaft 10. The higher stiffness of the tube 20 than that of the shaft 10 can improve the pushability and torque transmission of the balloon catheter 1. The higher stiffness of the tube 20 is also advantageous for improving the trackability of the balloon catheter 1, as the balloon catheter 1 can be configured to be stiffer than specified even if the outer diameter of the shaft 10 is reduced.

The stiffness of the tube 20 may be lower than the stiffness of the shaft 10. The stiffness of the tube 20 can be made lower than the stiffness of the shaft 10 by constructing the tube 20 from a resin that can provide lower stiffness than the resin constituting the shaft 10, or by making the wall thickness of the tube 20 thinner than the wall thickness of the shaft 10. The lower stiffness of the tube 20 than that of the shaft 10 can improve flexibility to improve trackability of the balloon catheter 1.

As shown in FIG. 5, in a cross-section perpendicular to the longitudinal axis direction x, preferably, the shaft 10 has a third position S3 where the lumen 100 of the shaft 10 is at its minimum width in the direction parallel to the straight line L2 by the restriction part 40, L3 is a line segment connecting opposing inner walls of the lumen of the shaft 10 at the third position S3 and being parallel to the straight line L2, and the outer edge of the tube 20 either contacts the line segment L3 or has a portion located on the opposite side of the figure center P2 of the outer edge of the tube 20 with respect to the line segment L3. In other words, the outer edge of the tube 20 preferably has a portion that is tangential to the line segment L3 or protrudes to the side of the first lumen 110 relative to the line segment L3. Since the position where the lumen 100 of the shaft 10 is at its minimum width in the direction parallel to the straight line L2 by the restriction part 40 is the position where the most protruding portion 41 of the restriction part 40 is present, the line segment L3 can be said to be a line segment connecting the most protruding portion 41 of the restriction part 40 provided on one side of the lumen 100 of the shaft 10 with respect to the straight line L1 and the most protruding portion 41 of the restriction part 40 provided on the other side with respect to the straight line L1.

The above configuration makes it easier to accommodate the guidewire 50 in the first lumen 110 and prevents entanglement between the guidewire 50 and the tube 20. In the above configuration, as shown in FIG. 5, the outer shapes of the tube 20 and the guidewire 50 in a cross-section perpendicular to the longitudinal axis direction x are preferably both circular. With such a configuration, the guidewire 50 inserted in the first lumen 110 and the outer wall of the tube 20 can make point contact in a cross-section perpendicular to the longitudinal axis direction x, and thus, reducing the resistance against the guidewire 50 when sliding in the first lumen 110 and improving the sliding property of the guidewire 50.

Alternatively, in the case where the restriction part 40 is provided only on one side with respect to the straight line L1, when L3 is defined as a line segment connecting the restriction part 40 on the one side at the third position S3 and the wall of the lumen 100 of the shaft 10 on the other side and being parallel to the straight ling L2, and the outer edge of the tube 20 either contacts the line segment L3 or has a portion located on the opposite side of the figure center P2 of the outer edge of the tube 20 with respect to the line segment L3.

While FIG. 5 shows an embodiment where the shaft 10 has the restriction part 40 formed by a thicker wall thickness of the shaft 10 between the first position S1 and the second position S2 than a wall thickness of the shaft 10 at the second position S2, even if the restriction part 40 is provided as a different member as shown in FIG. 2, the third position S3 can be defined as the position at which the lumen 100 of the shaft 10 is at its minimum width in the direction parallel to the straight line L2 by the restriction part 40, which is provided as a different member. L3 can be defined as the line segment connecting the opposing restriction parts 40 at the third position S3 and being parallel to the straight line L2, and the outer edge of the tube 20 preferably either contacts the line segment L3 or has a portion located on the opposite side of the figure center P2 of the outer edge of the tube 20 with respect to the line segment L3.

Alternatively, in the case where the restriction part 40 that is formed as a different member is disposed only on one side with respect to the straight line L1, L3 is a line segment connecting the restriction part 40 on the one side and the wall of the lumen 100 of the shaft 10 on the other side at the third position S3 and being parallel to the straight line L2, the outer edge of the tube 20 preferably either contacts the line segment L3 or has a portion located on the opposite side of the figure center P2 of the outer edge of the tube 20 with respect to the line segment L3.

As shown in FIG. 6, in a cross-section perpendicular to the longitudinal axis direction x, the shaft 10 has the third position S3 where the lumen 100 of the shaft 10 is at its minimum width in the direction parallel to the straight line L2 by the restriction part 40, L3 is the line segment connecting opposing inner walls of the lumen of the shaft 10 at the third position S3 and being parallel to the straight line L2, and the outer edge of the tube 20 may not have a portion located on the opposite side of the figure center P2 with respect to the line segment L3. In other words, the outer edge of the tube 20 preferably has no portion protruding toward the side of the first lumen 110 relative to the line segment L3.

To achieve the above configuration, as shown in FIG. 6, in a cross-section perpendicular to the longitudinal axis direction x, the first lumen 110 is preferably circular and the tube 20 preferably has a concave shape at the portion facing the first lumen 110, and the second lumen 120 preferably has a shape that along the outer shape of the tube 20 so that the above predetermined gap 200 can be formed. With such a configuration, the center of the guidewire 50 inserted into the first lumen 110 can be positioned close to the figure center P1 of the outer edge of the shaft 10 in a cross-section perpendicular to the longitudinal axis direction x, which brings the central axis of the guidewire 50 and the central axis of the shaft 10 close together and facilitates pushing the balloon catheter 1 along the guidewire 50 in the body cavity, thereby improving the pushability of the balloon catheter 1.

Alternatively, in the case where the restriction part 40 is disposed only on one side with respect to the straight line L1, L3 is a line segment connecting the restriction part 40 on the one side and the wall of the lumen 100 of the shaft 10 on the other side at the third position S3 and being parallel to the straight line L2, and the outer edge of the tube 20 preferably has a portion that is tangential to the line segment L3 or present on the opposite side of the figure center P2 of the outer edge of the tube 20 with respect to the line segment L3.

While FIG. 6 shows an embodiment where the shaft 10 has the restriction part 40 formed by a thicker wall thickness of the shaft 10 between the first position S1 and the second position S2 than the wall thickness of the shaft 10 at the second position S2, even if the restriction part 40 is provided as a different member as shown in FIG. 2, the third position S3 can be defined as the position at which the lumen 100 of the shaft 10 is at its minimum width in the direction parallel to the straight line L2 by the restriction part 40, which is provided as a different member. L3 can be defined as the line segment connecting the opposing restriction parts 40 at the third position S3 and being parallel to the straight line L2, and the outer edge of the tube 20 preferably has no portion located on the opposite side of the figure center P2 of the outer edge of the tube 20 with respect to the line segment L3.

Alternatively, in the case where the restriction part 40 that is provided as a different member is disposed only on one side relative to the straight line L1, L3 is a line segment connecting the restriction part 40 on the one side and the wall of the lumen 100 of the shaft 10 on the other side at the third position S3 and being parallel to the straight line L2, and the outer edge of the tube 20 preferably either connect the line segment L3 or has a portion on the opposite side of the figure center P2 of the outer edge of the tube 20 with respect to the line segment L3.

A portion of the outer wall of the tube 20 facing the first lumen 110 is preferably provided with a hydrophilic or hydrophobic coating. Since the portion of the outer wall of the tube 20 facing the first lumen 110 is the portion that the guidewire 50 inserted into the first lumen 110 may come in contact with, the coating on this portion can enhance the sliding property of the guidewire 50. The hydrophilic or hydrophobic coating can be applied by dipping the tube 20 into a hydrophilic or hydrophobic coating agent, spreading a hydrophilic or hydrophobic coating agent on the outer wall of the tube 20, or coating the outer wall of the tube 20 with a hydrophilic or hydrophobic coating agent. Depending on the material forming the guidewire 50, a coating agent can be selected that can reduce resistance to the material.

Hydrophilic coating agents that can be applied to the portion of the outer wall of the tube 20 facing the first lumen 110 include hydrophilic polymers such as polyvinyl alcohol, polyethylene glycol, polyacrylamide, polyvinyl pyrrolidone, methyl vinyl ether maleic anhydride copolymer; and hydrophilic coating agents made of any combination thereof.

Hydrophobic coating agents that can be applied to the portion of the outer wall of the tube 20 facing the first lumen 110 include polytetrafluoroethylene (PTFE), ethylene-propylene fluoride (FEP), silicone oil, hydrophobic urethane resin, carbon coat, diamond coat, diamond-like carbon (DLC) coating, ceramic coating, and substances with low surface free energy terminated with an alkyl group or a perfluoroalkyl group.

The wall of the lumen 100 of the shaft 10 forming the first lumen 110 is preferably provided with a hydrophilic or hydrophobic coating. Since the wall of the lumen 100 of the shaft 10 forming the first lumen 110 is the portion that the guidewire 50 inserted into the first lumen 110 may come in contact with, the coating on this portion can enhance the sliding property of the guidewire 50. The hydrophilic or hydrophobic coating can be applied by dipping the shaft 10 into a hydrophilic or hydrophobic coating agent, spreading a hydrophilic or hydrophobic coating agent on the wall of the lumen 100 of the shaft 10, or coating the wall of the lumen 100 of the shaft 10 with a hydrophilic or hydrophobic coating agent. Depending on the material forming the guidewire 50, a coating agent can be selected that can reduce resistance to the material. As for hydrophilic or hydrophobic coating agents available for the wall of the lumen 100 of the shaft 10 forming the first lumen 110, the hydrophilic or hydrophobic coating agents that can be applied to the portion of the outer wall of the tube 20 facing the first lumen 110 can be referred to.

The inner wall of the tube 20 is preferably provided with a hydrophilic or hydrophobic coating. The hydrophilic or hydrophobic coating can be applied by dipping the tube 20 into a hydrophilic or hydrophobic coating agent, spreading a hydrophilic or hydrophobic coating agent on the inner wall of the tube 20, or coating the inner wall of the tube 20 with a hydrophilic or hydrophobic coating agent. Depending on the type of fluid to be passed through the lumen of the tube 20, a coating agent can be selected that can reduce resistance to the fluid. This allows the fluid to easily pass through the lumen of the tube 20. As for hydrophilic or hydrophobic coating agents available for the inner wall of the tube 20, the hydrophilic or hydrophobic coating agents that can be applied to the portion of the outer wall of the tube 20 facing the first lumen 110 can be referred to.

A portion of the outer wall of the tube 20 facing the second lumen 120 is preferably provided with a hydrophilic or hydrophobic coating. The hydrophilic or hydrophobic coating can be applied by dipping the tube 20 into a hydrophilic or hydrophobic coating agent, spreading a hydrophilic or hydrophobic coating agent on the outer wall of the tube 20, or coating the outer wall of the tube 20 with a hydrophilic or hydrophobic coating agent. Since the portion of the outer wall of the tube 20 facing the second lumen 120 is the portion that forms the gap 200, the coating agent applied on this portion can adjust the amount of residual water retained after flushing in the gap 200. When a hydrophilic coating agent is used, water can be retained in the gap 200 because the hydrophilic coating agent is wetted. When a hydrophobic coating agent is used, the residual water after flushing is not easily absorbed by the tube 20, allowing the gap 200 to retain moisture efficiently and the retained water to easily seep into the first lumen 110.

As shown in FIG. 1, the balloon catheter 1 may have a hub 4 at a proximal side of the shaft 10, and the hub 4 may be provided with a fluid inlet 2 and a guidewire insertion port 3. The balloon catheter 1 having the hub 4 provided with the fluid inlet 2 and the guidewire insertion port 3 can facilitate the operation of supplying fluid inside the balloon 30 to inflate or deflate the balloon 30 and the operation of the guidewire 50. The balloon catheter 1 in accordance with embodiments of the present invention can be applicable to not only the one of so-called over-the-wire type shown in FIG. 1, in which the guidewire 50 is inserted over the distal to proximal side of the shaft 10, but also a so-called rapid-exchange type, in which the guidewire 50 is inserted from the distal side to the midway of the proximal side of the shaft 10.

The shaft 10 and the hub 4 may be joined by, for example, adhesive bonding or welding. Of these, the shaft 10 and the hub 4 are preferably joined by adhesive bonding. The adhesive bonding of the shaft 10 and the hub 4 can increase the bonding strength even when the materials forming the shaft 10 and the hub 4 are different, for example, in a case where the shaft 10 is made of material having high flexibility and the hub 4 is made of material having high stiffness, and thus increasing the degree of freedom in the selection of materials constituting the shaft 10 and the hub 4.

Although not shown in the figures, the balloon catheter 1 preferably has a tip member at the distal end. The tip member can prevent damage a living organ such as a vessel wall and the lumenal wall of an organ when the distal end of the balloon catheter 1 contacts the living organ.

The present application claims priority based on Japanese Patent Application No. 2022-23390 filed on Feb. 18, 2022. All the contents described in Japanese Patent Application No. 2022-23390 filed on Feb. 18, 2022 are incorporated herein by reference.

DESCRIPTION OF REFERENCE SIGNS

1: balloon catheter
2: fluid inlet
3: guidewire insertion port
4: hub
10: shaft
20: tube
30: balloon
40: restriction part
41: most protruding portion
50: guidewire
100: lumen of the shaft
110: first lumen
120: second lumen
200: gap
P1: figure center of the outer edge of the shaft
P2: figure center of the outer edge of the tube
L1: straight line connecting P1 and P2
L2: straight line passing through P2 and being parallel to L1
L3: line segment
S1: first position
S2: second position
S3: third position
$W_{20}$: length defined by the outer edge of the tube
$W_{200}$: total length of the gap
x: longitudinal axis direction
y: radial direction

The invention claimed is:

1. A balloon catheter having a distal end and a proximal end in a longitudinal axis direction, comprising:

a shaft having a lumen and extending in the longitudinal axis direction, the lumen of the shaft including a first lumen through which a guidewire is to be inserted and a second lumen extending in the longitudinal axis direction;

a balloon disposed at a distal part of the shaft; and a tube disposed in the second lumen, wherein in a cross-section perpendicular to the longitudinal axis direction, the first lumen and the second lumen are in communication with each other;

the shaft has, in the lumen, a restriction part preventing the tube from moving from the second lumen to the first lumen;

an outer periphery of the shaft is continuous in a circumferential direction in a cross-section perpendicular to the longitudinal axis direction;

a distal part of the tube is connected to a proximal end part of the balloon so that the tube is a flow path for fluid that is introduced to inflate the balloon;

the balloon catheter has a gap between an outer wall of the tube and a wall of the second lumen, wherein the tube is disposed in the second lumen so that the outer wall of the tube does not contact with the wall of the second lumen to form the gap, and the gap is in communication with the first lumen; and a total length of the gap is equal to or shorter than a length defined by an outer edge of the tube on a straight line L2 in the cross-section perpendicular to the longitudinal axis direction, where L1 is a straight line connecting a figure center P1 of an outer edge of the shaft and a figure center P2 of the outer edge of the tube, and the straight line L2 is a straight line passing through the figure center P2 and being perpendicular to the straight line L1.

2. The balloon catheter according to claim 1, wherein in the cross-section perpendicular to the longitudinal axis direction, the restriction part is disposed between a first position where the largest diameter of the first lumen is located and a second position where the largest diameter of the second lumen is located in a direction parallel to the straight line L2, and a thickness of the restriction part is thicker than a thickness of the shaft at the second position in the direction parallel to the straight line L2, so that the restriction part prevents the tube from moving from the second lumen to the first lumen.

3. The balloon catheter according to claim 1, wherein the shaft and the tube are formed from different materials.

4. The balloon catheter according to claim 1, wherein a stiffness of the tube is higher than a stiffness of the shaft.

5. The balloon catheter according to claim 1, wherein a stiffness of the tube is lower than a stiffness of the shaft.

6. The balloon catheter according to claim 1, wherein in the cross-section perpendicular to the longitudinal axis direction, the shaft has the restriction part at a third position where the restriction part forms a minimum width of the lumen of the shaft in a direction parallel to the straight line L2, and the outer edge of the tube either contacts a line segment L3 or has a portion located on the opposite side of the figure center P2 with respect to the line segment L3, where the line segment L3 is a line segment connecting opposing inner walls of the lumen of the shaft at the third position and being parallel to the straight line L2.

7. The balloon catheter according to claim 1, wherein in the cross-section perpendicular to the longitudinal axis direction, the shaft has the restriction part at a third position where the restriction part forms a minimum width of the lumen of the shaft in a direction parallel to the straight line L2, and the outer edge of the tube does not have a portion located on the opposite side of the figure center P2 with respect to a line segment L3, where the line segment L3 is a line segment connecting opposing inner walls of the lumen of the shaft at the third position and being parallel to the straight line L2.

8. The balloon catheter according to claim 1, wherein a portion of the outer wall of the tube facing the first lumen is provided with a hydrophilic or hydrophobic coating.

9. The balloon catheter according to claim 1, wherein an inner wall of the shaft forming the first lumen is provided with a hydrophilic or hydrophobic coating.

10. The balloon catheter according to claim 1, wherein an inner wall of the tube is provided with a hydrophilic or hydrophobic coating.

11. The balloon catheter according to claim 1, wherein the straight line L1 crosses the first lumen in a cross-section perpendicular to the longitudinal axis direction.

12. The balloon catheter according to claim 1, wherein the outer periphery of the shaft is continuous in the circumferential direction in the cross-section perpendicular to the longitudinal axis direction so that the shaft does not have a slit in the outer periphery.

* * * * *